United States Patent [19]

Pizzino

[11] Patent Number: 4,702,737
[45] Date of Patent: Oct. 27, 1987

[54] DUAL DOSE SYRINGE

[76] Inventor: Joanne L. Pizzino, 1426 Sugar Knoll Dr., Akron, Ohio 44313

[21] Appl. No.: 885,416

[22] Filed: Jul. 14, 1986

[51] Int. Cl.⁴ .............................................. A61M 5/08
[52] U.S. Cl. ................................................... 604/191
[58] Field of Search .................. 604/191, 88, 86, 87, 604/187, 218, 232, 234, 188, 221, 222, 224

[56] References Cited

U.S. PATENT DOCUMENTS

| | | | |
|---|---|---|---|
| 2,453,591 | 11/1948 | Poux | 604/232 |
| 2,939,459 | 6/1970 | Lazarte et al. | 604/191 |
| 3,911,916 | 10/1975 | Stevens . | |
| 3,923,058 | 3/1975 | Weingarten . | |
| 3,946,732 | 3/1976 | Hurscham | 604/88 |
| 4,171,698 | 10/1979 | Genese | 604/88 |
| 4,313,440 | 2/1982 | Ashley | 604/191 |
| 4,424,057 | 1/1984 | House | 604/88 |
| 4,439,184 | 5/1984 | Wheeler . | |

*Primary Examiner*—John D. Yasko
*Attorney, Agent, or Firm*—Oldham, Oldham & Weber Co.

[57] ABSTRACT

A multiple dose, single barrel syringe has a barrel comprising a plurality of telescoping sections of progressively decreasing diameter. A puncturable fluid tight membrane extending across the forward end of each barrel section except the first divides the interior of the barrel into a plurality of separate fluid receiving chambers, each of which may contain a different fluid medication. A plunger is slidably mounted in the last barrel section and extends exteriorly therefrom. At the forward end of the syringe is a hollow needle, which extends through a needle-receiving tubular conduit at the forward end of the first barrel section so that the needle is disposed partly inside and partly outside the barrel. Both ends of the needle are sharply pointed. The inner end of the needle punctures the membranes so that, as each chamber in the barrel is emptied, the next chamber is placed in communication with the needle.

15 Claims, 2 Drawing Figures

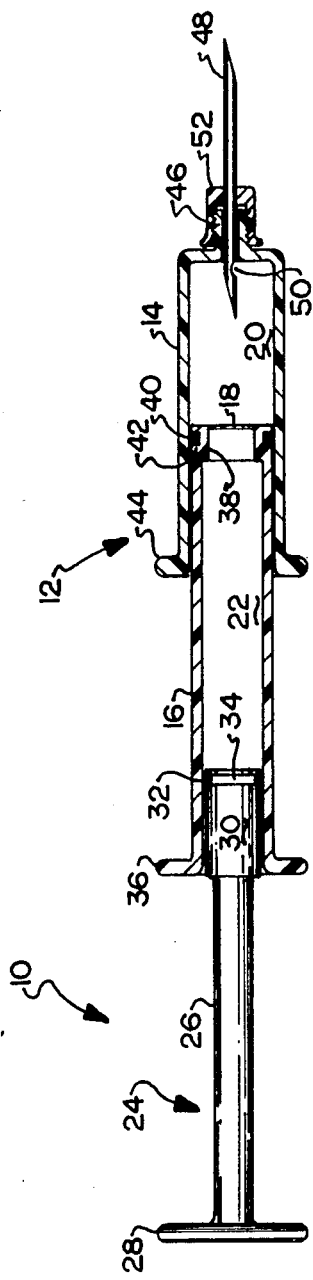
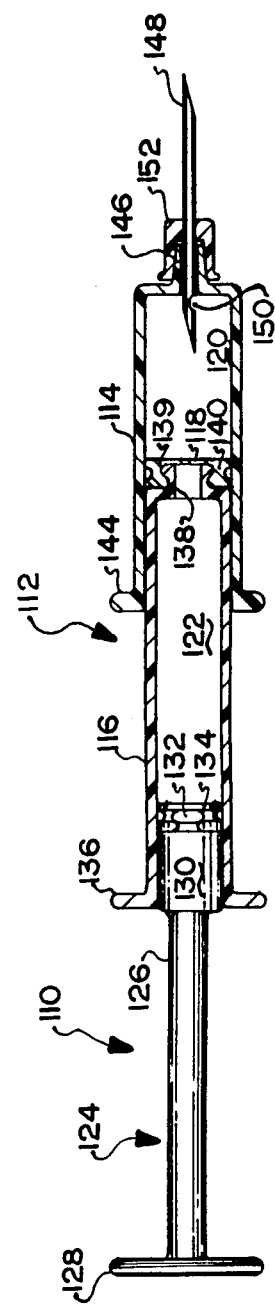
FIG. 1
FIG. 2

DUAL DOSE SYRINGE

TECHNICAL FIELD

This invention relates to syringes for medical purposes, and more particularly to multiple dose, single barrel syringes.

BACKGROUND ART

Single barrel syringes for sequential injection of two or more fluid medications are known. These syringes generally include one or more floating plugs or pistons which divide the interior of the syringe barrel into chambers for different fluid medications. Examples of such multiple dose, single barrel syringes are shown in U.S. Pat. Nos. 3,911,916 to Stevens, 3,923,058 to Weingarten, and 4,439,184 to Wheeler. Despite the obvious advantages (particularly patient comfort) in using a single syringe capable of delivering two or more medications sequentially, instead of using separate syringes for each medication, multiple dose syringes have not enjoyed wide-spread use. There are several reasons why multiple dose, single barrel syringes have not become commercially successful. First of all, the floating plug(s) may tilt. This may happen either when one draws back the plunger to aspirate a small amount of blood from the patient, or when one presses the plunger forward to expel fluid. In either case, tilting of the plug greatly increases friction and makes it very difficult to press the plunger forward in order to expel fluid. This tilting also makes it very difficult to aspirate, since tilting is very likely to occur during aspiration. The second problem is that the plug, in order to be fluid tight (which it must be), has a rather high friction resistance against the barrel wall even when it does not tilt. The third problem is that these plugs, which are generally of substantial thickness, offer considerable resistance to puncturing by the needle. Each plug must be punctured in turn by the needle as the chamber on the forward or distal side of the plug is empty, in order to place the next chamber in communication with the needle. Difficulty in puncturing the plug poses a considerable obstacle to successfull use of the syringe.

Syringes having two or more barrels and a single needle for injecting a plurality of fluid medications are also known. The multiple barrel arrangement avoids the difficulties associated with the floating plugs in single barrel, multiple dose syringes. However, the multiple barrel syringes, even when only two barrels are present, are relatively bulky and difficult to use. Such syringes likewise have not enjoyed any appreciable commercial use.

DISCLOSURE OF THE INVENTION

It is an object of this invention to provide a multiple dose syringe which is easy to use.

It is an object of this invention to provide a multiple dose syringe in which the dividers that separate adjacent fluid chambers are easily punctured by a needle.

It is a further object of this invention to provide a multiple dose, single barrel syringe which utilizes thin membranes instead of plugs to separate adjacent fluid chambers.

A still further object of this invention is to provide a multiple dose syringe which permits the user to aspirate blood.

This invention provides a novel, multiple dose, single barrel syringe which has a barrel comprising a plurality of telescoping sections of progressively decreasing diameter, and a puncturable fluid tight membrane extending across the forward end of each barrel section except the first, dividing the interior of the barrel into a plurality of separate fluid receiving chambers. This syringe also includes a plunger received in the last barrel section and extending exteriorly thereof, sealing means providing fluid tight seals between successive barrel sections and between the last barrel section and the plunger, and a hollow needle extending through needle receiving means at the forward end of the first barrel section.

BRIEF DESCRIPTION OF DRAWINGS

In the Drawings:

FIG. 1 is a longitudinal sectional view of a syringe according to a first embodiment of this invention, with the plunger shown in elevation.

FIG. 2 is a longitudinal sectional view of a syringe according to a second embodiment of this invention, with the plunger shown in elevation.

BEST MODE FOR CARRYING OUT INVENTION

This invention will now be described in detail with reference to the specific embodiments thereof. Both embodiments illustrated are dual dose syringes, but it will be apparent that the principles thereof are also applicable to single barrel syringes capable of dispensing three or more fluid medications.

A first embodiment of this invention is shown in FIG. 1. Referring now to FIG. 1, 10 indicates the syringe of this first embodiment as a whole. Syringe 10 has a barrel 12 which comprises sections 14 and 16, the latter being of smaller diameter than the former and telescoping within the former. A thin, puncturable, fluid tight membrane 18, typically about 0.002 inch thick, extends across the forward end of barrel section 16, dividing the interior of barrel 12 into separate fluid receiving chambers 20 and 22.

Plunger 24 is slidably mounted in second barrel section 16. A portion of plunger 24 extends exteriorly of barrel 12. Plunger 24 includes a cylindrical shaft 26, a thumb pad 28 at its outer end, and a cylindrical forward portion 30, which may be of larger diameter than the remainder of shaft 26. An O-ring 32 of elastomeric material, situated in a groove 34 in forward portion 30, provides a fluid tight seal between plunger 24 and the interior wall of barrel section 16.

The second barrel section 16 has a finger piece 36 at its back end. Finger piece 36 may consist of a pair of diametrically opposite ears. At the forward end of barrel section 16 is a forward portion 38 of smaller internal diameter than but the same external diameter as the remainder of barrel section 16. This provides a greater wall thickness. An elastomeric O-ring 40, situated in groove 42 in forward portion 38, provides a fluid tight seal between barrel sections 14 and 16. Membrane 18 extends across the forward end of forward portion 38 and is integrally joined thereto. Second fluid chamber 22 is enclosed between membrane 18 and the forward end of plunger 24.

First barrel section 14 has a finger piece 44 (e.g. a pair of diametrically opposite ears) at its back end. At the front end of barrel section 14 is a short, externally screw threaded tubular conduit 46 which serves as needle receiving means. A double ended hollow needle 48, sharply pointed at both ends, extends through conduit 46 so that part of the needle lies inside barrel 12 and part lies outside. The portion of needle 48 that lies inside barrel 12 has an opening 50 near the forward end of barrel section 14. This portion of needle 48 must be of sufficient length to puncture membrane 18 as second barrel section 16 approaches the forward limit of its travel. An internally screw threaded hub 52, which may be permanently secured to needle 48, permits attachment of the needle to barrel 12 via conduit 46.

A protective cap (not shown) which overlies needle 48 and hub 52, is normally provided in order to maintain sterility of the needle and to prevent accidental puncture of a person by the needle.

A second embodiment of the syringe of this invention will now be described with reference to FIG. 2. The second embodiment differs from the first in the sealing means between the plunger and the second barrel section and between the two barrel sections, and also differs in the structure for attachment of the needle and hub to the syringe. Otherwise the two embodiments are structurally similar.

Referring now to FIG. 2, syringe 110 according to the second embodiment comprises a barrel 112 having two sections 114 and 116, the latter being of smaller diameter than and telescoping within the former. A membrane 118 extends across the forward end of barrel section 116, dividing the interior of barrel 112 into first and second fluid chambers 120 and 122, respectively.

Syringe 110 has a plunger 124 which is slidably mounted in barrel section 116. A portion of plunger 124 extends exteriorly of barrel 112. Plunger 124 includes a thumb pad 128 and a cylindrical forward portion 130 which may be of larger diameter than the remainder of shaft 126. The knob 132 projects forwardly from the forward end of forward portion 130. A sealing member 134, which comprises an integral thin membrane and snap ring portion, 140 is removably secured to plunger 124 via knob 132. The lateral portions of this sealing member 134 provides a fluid tight seal between plunger 124 and the interior wall of barrel section 116. Sealing member 134 is preferably made of an elastomeric material, such as natural or synthetic rubber.

The second barrel section 116 includes a finger piece 136 at its back end, and a tubular forward portion 138 which is smaller in both inside and outside diameter than the remainder of barrel section 116. A lip 139 is provided at the tip end of forward portion 138. A snap ring 140, which is attached to membrane 118, is removably secured to barrel section 116 via forward portion 138. Snap ring 140 provides a seal between barrel sections 114 and 116. Membrane 118 and snap ring 140 are preferably formed as a single piece of elastomeric material. Elastomeric material is desired both for sealing action and to permit snap ring 140 to be deformed temporarily as it is snapped into place over lip 139. It will be observed that membrane 118 is removably secured to barrel section 116 in this embodiment, while its counterpart membrane 18 in FIG. 1 is permanently attached to barrel section 16.

First barrel section 114 comprises finger piece 144 at its back end, and a forwardly projecting tubular conduit 146 at its front end. Conduit 146 provides needle receiving means for receiving a do2uble ended hollow needle 148, which may be identical to its counterpart 48 in FIG. 1. Thus, needle 148 has an opening 150 near the forward end of barrel section 114. A hub 152 may be permanently attached to needle 148. Hub 152 and conduit 146 have mating surfaces which may be slightly tapered as shown; however, these surfaces, unlike their counterparts in FIG. 1, are not screw threaded. An adhesive may be provided on these surfaces if desired to secure needle 148 permanently to syringe 110. A cap (not shown) may overlie needle 148 and hub 152.

Except for elastomeric seals 32, 40, 132 and 140 and stainless steel needles 48 and 148, the syringes according to either embodiment of the invention are preferably made of a colorless, transparent or translucent material. Polypropylene is preferred; other pharmaceutically acceptable plastic materials or glass may also be used. Plastic materials, and particularly polypropylene, are preferred because of their lower resistance to breakage.

The syringes of this invention are preferably disposable, (i.e. single use) syringes which are pre-filled with the desired injectable fluid medications. Where injection into a patient in a predetermined sequence is important, the first fluid to be injected is contained in first chamber 20 or 120, and the second fluid medication to be injected is contained in second chamber 22 or 122. By way of example, the syringe according to this invention may be used for the injection of saline solution followed by heparin solution to a heparin lock. Heparin locks are commonly used when repeated intravenous administration of fluids (such as glucose or an antibiotic) is required, and it is necessary to administer heparin periodically to maintain patency. Other instances in which administration of two fiuids is required are well known, and the syringes of this invention may be used in those cases also.

Difficulties in refilling the syringes of this invention, particularly any chamber thereof except the first, under sterile conditions in a hospital or physician's office, militates against the reuse of syringes of this invention. These syringes can be reused, however, where appropriate materials (preferably glass) are used to make the syringe and where the needle and its hub are detachable from the syringe, as shown in FIG. 1, and when sterile conditions are maintained.

Various modifications can be made without departing from the scope and spirit of this invention.

A syringe of this invention may have more than two barrel sections if desired. In this case each barrel section except the first has a fluid tight membrane similar to membrane 18 or 118 extending across the forward end thereof, and sealing means such as O-ring 40 or snap ring 140 are provided at the forward end of each barrel section except the first in order to provide seals between successive barrel sections, and between the last barrel section and the plunger. The plunger is received in the last barrel section and extends exteriorly thereof. The barrel sections are telescoping and are of progressively decreasing diameter. As a practical matter, it is not feasible to provide more than 3 or 4 barrel sections (and correspondingly 3 or 4 fluid chambers) because the last barrel section will be quite small in diameter and must be of correspondingly long length in order to hold the required fluid volume. Also, small barrel diameter would require a greater than desirable force exerted on plunger 24 or 124 in order to expel fluid. The portion of needle 48 or 148 which is inside barrel 12 or 112 must be long enough to puncture each membrane 18 or 118; the length of needle required becomes longer with each additional fluid reciving chamber.

Either form of joint between hub 52 or 152 and conduit 46 or 146 can be used with either form of sealing means.

Other modifications will also be apparent to those skilled in the art.

Syringes of this invention can be used for any of the usual modes of injection of fluids, e.g. intravenous, intramuscular, or subcutaneous injection. The patient can be either a human or other warm blooded animal.

By way of specific example, the dimensions of syringe according to either embodiment containing 1 cubic centimeter of fluid in each chamber 20 and 22 or 120 and 122 may be as shown in Table 1 below. All dimensions are in centimeters. The abbreviations "I.D." and "O.D." denote inside diameter (or bore) and outside diameter respectively.

TABLE 1

|  | I.D. | O.D. | Stroke |
|---|---|---|---|
| Barrel |  |  |  |
| First Section | 0.814 | 1.100 | 1.920 |
| Second Section | 0.564 | 0.764 | 4.000 |
| Plunger | — | 0.560 | 5.500 |

It will be appreciated that any additional barrel sections in a syringe having 3 or more such sections would be longer and correspondingly of smaller diameter.

Syringes of this invention are typically shorter and of greater diameter than typical syringes holding the same volume of fluid in a single chamber (e.g, a 2 cc syringe). However, the length and diameter of the syringes of this invention can be varied as desired.

Operation of the syringe according to this invention will now be described. Since the syringes of both embodiments operate in the same way, the description will be directed to use of the syringe shown in FIG. 1.

As indicated previously, the syringe is preferably pre-filled at the factory. To use the syringe of this invention, one inserts the needle 48 into the patient, e.g., into a vein or a muscle or under the skin thereof. For intravenous injection, it is desirable to aspirate a small quantity of blood by drawing back on the plunger 24 in the usual manner. To aspirate, the user may place two fingers (e.g. the index and middle finger of the left hand) against finger piece 44 to hold first section 14 while simultaneously pulling back second section 16 by engaging finger pieces 36 with the right hand. Then the user presses plunger 24 forward, expelling fluid from first chamber 20 until this chamber has been emptied. When chamber 20 has been nearly emptied, continued pushing forward of plunger 24 will cause membrane 18 to be punctured by the inner end of needle 48. As this is happening the small remaining quantity of fluid in chamber 20 will be expelled through opening 50. When membrane 18 has been punctured, continuing forward motion of plunger 24 causes fluid to be expelled from the second chamber 22 into needle 48. One continues to push plunger 24 forward until the forward end of the plunger touches needle 48, at which time substantially all the fluid in chamber 22 has been expelled.

Where more than two barrel sections are present, one pushes plunger 24 forward until all barrel sections have been emptied. Each membrane 18 is punctured by needle 48 as the chamber in the preceding section is emptied. Of course, the portion of needle 48 which lies inside barrel 12 must be long enough to puncture all membranes 18. It will be appreciated that a considerably greater length of needle inside the barrel is required where there are 3 or more barrel sections than is required where there is only 2.

Syringes of this invention have several advantages over multiple dose syringes presently known in the art.

First, syringes of the present invention are capable of aspirating. This is not the case with single barrel, multiple dose syringes employing floating plugs to separate adjacent fluid chambers. Secondly, membrane 18 (or 118) of this invention is much more easily punctured by the needle than are the plugs used in presently known syringes, because the membrane herein is much thinner. At the same time, the membrane is strong enough so that it is not broken until the syringe is actually used. A third advantage is that the syringes of this invention can be used with much less effort than is the case with single barrel syringes employing plugs. This is because the barrel sections herein have no tendency to tilt, as do floating plugs, so that friction remains relatively small. In contrast, friction exerted by a floating plug which is tilted is considerable. Even when a floating plug has not tilted, the frictional resistance it exerts is considerably greater than the frictional resistance exerted by the seals herein.

Syringes of this invention are much less cumbersome and therefore much easier to use than multiple barrel (including 2 barrel) syringes.

Applicant has provided a simple, easy to use, multiple dose, single barrel syringe which makes it feasible to inject two or more fluid medications in sequence to a patient. At present a separate syringe is used for each fluid to be injected. The syringes of this invention thus result in a substantial increase in patient comfort, since only one puncture is necessary for a single course of injections, instead of a separate puncture for each fluid to be injected.

While in accordance with the patent statutes, a preferred embodiment and best mode has been presented, the scope of the invention is not limited thereto, but rather is measured by the scope of the attached claims.

What is claimed is:

1. A pre-filled multiple dose, single barrel syringe for dispensing at least two fluids in predetermined sequence, said syringe comprising:
    (a) a barrel comprising a plurality of telescoping sections of progressively decreasing diameter;
    (b) a thin puncturable fluid tight membrane extending across the forward end of each barrel section except the first and reciprocable therewith, said membrane dividing the interior of said barrel into a plurality of separate fluid-receiving chambers each of said chambers being pre-filled with a fluid;
    (c) a plunger received in the last barrel section and including a portion extending exteriorly of the barrel;
    (d) sealing means providing fluid tight seals between successive barrel sections and between the last barrel section and said plunger;
    (e) needle receiving means at the forward end of the first barrel section, and
    (f) a hollow meedle extending through said needle receiving means, said needle being sharply pointed at both ends, a portion of said needle being inside said barrel and a portion of said needle being outside said barrel.

2. A syringe according to claim 1 in which said barrel has two telescoping sections.

3. A syringe according to claim 1 in which said membrane is a plastic member.

4. A syringe according to claim 1 in which said membrane is integrally joined to said barrel section.

5. A syringe according to claim 4 in which said sealing means comprises a sealing ring and a groove in said barrel section therefor.

6. A syringe according to claim 1 in which said sealing means includes a snap ring removably secured to said barrel section, said membrane being integral with said snap ring.

7. A syringe according to claim 1 in which the portion of the needle inside the barrel has an opening near the forward end of said barrel.

8. A syringe according to claim 7 in which the portion of said needle inside said barrel is of sufficient length to puncture each of said membranes.

9. A syringe according to claim 1 in which said needle receiving means comprises a tubular conduit of reduced diameter.

10. A syringe according to claim 9 in which said needle has a hub joined thereto and said hub is received in said needle receiving means.

11. A syringe according to claim 10 in which said needle receiving means is externally screw threaded and said hub is internally screw threaded.

12. A syringe according to claim 1 in which said barrel sections are made of transparent or translucent plastic material.

13. A syringe according to claim 1, said syringe being disposable.

14. A syringe according to claim 1 in which said needle is fixedly positioned with respect to said barrel.

15. A syringe according to claim 1 in which the thickness of said membrane is in the order of about 0.002 inch.

* * * * *